United States Patent
Murata et al.

(10) Patent No.: US 7,728,149 B2
(45) Date of Patent: Jun. 1, 2010

(54) PROCESS FOR PRODUCING DICARBOXYLIC ACID

(75) Inventors: Kiyokazu Murata, Himeji (JP); Hiroyuki Miura, Takasago (JP)

(73) Assignee: Daicel Chemical Industries, Ltd., Osaka (JP)

(*) Notice: Subject to any disclaimer, the term of this patent is extended or adjusted under 35 U.S.C. 154(b) by 1009 days.

(21) Appl. No.: 10/498,048

(22) PCT Filed: Jan. 14, 2003

(86) PCT No.: PCT/JP03/00189

§ 371 (c)(1),
(2), (4) Date: Jun. 9, 2004

(87) PCT Pub. No.: WO03/064365

PCT Pub. Date: Aug. 7, 2003

(65) Prior Publication Data

US 2005/0080289 A1    Apr. 14, 2005

(30) Foreign Application Priority Data

Jan. 29, 2002  (JP) .............................. 2002-020617

(51) Int. Cl.
*C07C 51/16* (2006.01)
*C07F 15/06* (2006.01)

(52) U.S. Cl. ........................... 548/402; 546/2; 562/542

(58) Field of Classification Search ................... 546/2; 548/402; 562/542

See application file for complete search history.

(56) References Cited

U.S. PATENT DOCUMENTS 4,032,569 A * 6/1977 Onopchenko et al. ....... 562/543
7,015,356 B2 * 3/2006 Ishii et al. ................... 562/549

FOREIGN PATENT DOCUMENTS

EP   0 824 962 A1   2/1998
GB   1161191 A      8/1969

OTHER PUBLICATIONS

Yuukikasankabutsu (1972) (Organic Peroxide—Its Chemistry and Industrial Utilization) Publisher: Kabushikighaisya Kagakukougyousya.

* cited by examiner

*Primary Examiner*—Yong Chu
(74) *Attorney, Agent, or Firm*—Birch, Stewart, Kolasch & Birch LLP

(57) ABSTRACT

A process produces a corresponding dicarboxylic acid by subjecting a cycloalkane to an oxidative cleavage reaction with oxygen in the presence of a catalyst in a liquid phase using a continuous reactor, in which a residence time $\tau$ (hr) satisfies the following condition: $0.1 \leq \tau \leq 50/c$, wherein c is the proportion (% by weight) of the cycloalkane to the total weight of a charged liquid. The catalyst includes, for example, cobalt compounds, manganese compounds, and mixtures of these compounds, as well as imide compounds having at least one cyclic imide skeleton.

4 Claims, No Drawings

PROCESS FOR PRODUCING DICARBOXYLIC ACID

This application is a 35 USC 371 national stage application of PCT/JP03/00189, filed Jan. 14, 2003, which claims priority of Japanese application JP 2002-20617, filed Jan. 29, 2002.

BACKGROUND OF THE INVENTION

1. Field of the Invention

The present invention relates to a process for producing a dicarboxylic acid. More specifically, it relates to a process for producing a dicarboxylic acid by subjecting a cycloalkane to an oxidative cleavage reaction with oxygen in the presence of a catalyst using a continuous reactor to thereby yield a corresponding dicarboxylic acid. Such dicarboxylic acids are useful as, for example, raw materials for polyamides and polyesters, additives for polymers, and intermediate materials for fine chemicals. Among them, adipic acid is typically important as a raw material for nylon 66 (polyamide 66).

2. Description of the Related Art

Certain processes of oxidatively cleaving a mixture of a cycloalkanone and a cycloalkanol are known as processes for producing dicarboxylic acids. For example, adipic acid, a raw material for polyamides, is produced by a process of converting cyclohexane by oxidation with air into a mixture of cyclohexanone and cyclohexanol, and oxidizing the mixture with nitric acid. However, this process invites large amounts of nitrogen oxides, which are believed to be global warming gases, during oxidation with nitric acid and requires enormous facilities and efforts for disposal of the nitrogen oxides.

As a possible solution to the problem, a process of directly oxidizing a cycloalkane with oxygen to thereby yield a corresponding dicarboxylic acid has been investigated as a process without by-production of nitrogen oxides. The process, if feasible, can markedly reduce production process steps and production cost of dicarboxylic acids.

For example, processes of oxidizing cyclohexane in one step to yield adipic acid have been studied since 1960s (e.g., Japanese Unexamined Patent Application Publication No. 49-100022, PCT International Publication No. WO 9407834, Japanese Patents No. 3197518 and No. 3056790). However, no plant has been launched in commercial production. The reasons are as follows. These processes have been conventionally studied mainly using batch-system reactors in which if the conversion from cyclohexane increases for increasing productivity of dicarboxylic acid, a reaction time increases, and the increased reaction time invites increased by-production of glutaric acid, succinic acid, and other dicarboxylic acids than the target adipic acid and increased by-production of esters, lactones, high-boiling compounds, and other by-products. Accordingly, the processes require complicated purification process steps, invite a decreased utilization of cyclohexane to thereby invite increased production cost of adipic acid. In addition, such by-products deteriorate the catalytic activity. Further, the batch-system reactors require excessively large cost of construction and equipment of plants and are low in operability in commercial production.

SUMMARY OF THE INVENTION

Accordingly, an object of the present invention is to provide a process for producing a corresponding dicarboxylic acid in a high space-time yield by catalytic oxidation of a cycloalkane with oxygen.

Another object of the present invention is to provide a process for producing a corresponding dicarboxylic acid by catalytic oxidation of a cycloalkane with oxygen with minimized deterioration in catalytic activity.

After intensive investigations to achieve the above objects, the present inventors have found that a target dicarboxylic acid can be produced in a high space-time yield by oxidative cleavage of a cycloalkane with oxygen in the presence of a catalyst using a continuous reactor for a specific residence time. The present invention has been accomplished based on these findings.

Specifically, the present invention provides a process for producing a dicarboxylic acid including the step of subjecting a cycloalkane to an oxidative cleavage reaction with oxygen in the presence of a catalyst in a liquid phase using a continuous reactor to thereby yield a corresponding dicarboxylic acid, in which a residence time $\tau$ (hr) satisfies the following condition:

$$0.1 \leq \tau \leq 50/c$$

wherein c is the proportion (% by weight) of the cycloalkane based on the total weight of a charged liquid.

As the catalyst, one of cobalt compounds, manganese compounds and mixtures of these compounds may be used. The catalyst may also be an imide compound having at least one cyclic imide skeleton represented by following Formula (I):

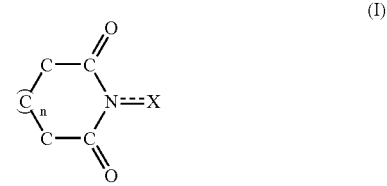

wherein n is 0 or 1; and X is an oxygen atom or a —OR group, wherein R is a hydrogen atom or a hydroxyl-protecting group. Such imide compounds include, for example, compounds represented by following Formula (1):

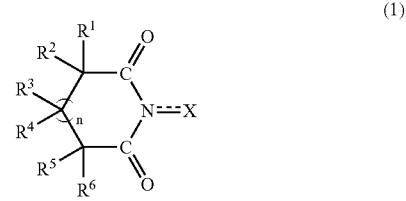

wherein n is 0 or 1;
X is an oxygen atom or a —OR group
wherein R is a hydrogen atom or a hydroxyl-protecting group;
$R^1$, $R^2$, $R^3$, $R^4$, $R^5$ and $R^6$ are the same or different and are each one selected from the group consisting of a hydrogen atom, halogen atoms, alkyl groups, aryl groups, cycloalkyl groups, hydroxyl group, alkoxy groups, carboxyl group, substituted oxycarbonyl groups, acyl groups, and acyloxy groups,
wherein at least two of $R^1$, $R^2$, $R^3$, $R^4$, $R^5$ and $R^6$ may be combined to form one of a double bond, an aromatic ring and a non-aromatic ring, and
wherein one or more of the N-substituted cyclic imido group indicated in Formula (1) may be formed on at least one of $R^1$, $R^2$, $R^3$, $R^4$, $R^5$ and $R^6$ and/or on the double bond, aromatic ring or non-aromatic ring formed by the at least two of $R^1$, $R^2$, $R^3$, $R^4$, $R^5$ and $R^6$.

A carboxylic acid can be used as a reaction solvent. A reaction temperature is preferably from 80° C. to 150° C., and a reaction pressure is preferably equal to or more than 0.5 MPa.

The process of the present invention can produce a corresponding dicarboxylic acid in a high space-time yield by catalytic oxidation of a cycloalkane with oxygen with minimized deterioration in catalytic activity.

Further objects, features and advantages of the present invention will become apparent from the following description of the preferred embodiments.

DESCRIPTION OF THE PREFERRED EMBODIMENTS

Cycloalkanes

Cycloalkanes (hereinafter briefly referred to as "substrate") are used as a raw material in the present invention.

Such cycloalkanes include, but are not limited to, cyclopropane, cyclobutane, cyclopentane, cyclohexane, cycloheptane, cyclooctane, cyclononane, cyclodecane, cyclododecane, cyclotetradecane, cyclohexadecane, cyclooctadecane, cycloicosane, cyclodocosane, cyclotriacontane, and other cycloalkanes each having from about 3 to about 30 members. Among them, cyclopentane, cyclohexane, cyclooctane, cyclododecane, and other cycloalkanes each having about 5 to about 15 members are preferred, of which cyclohexane and cyclododecane are typically preferred.

The cycloalkanes may have at least one substituent within ranges not adversely affecting the reaction. Such substituents include, but are not limited to, halogen atoms, oxo group, hydroxyl group, mercapto group, substituted oxy groups (e.g., alkoxy groups, aryloxy groups, and acyloxy groups), substituted thio groups, carboxyl groups, substituted oxycarbonyl groups, substituted or unsubstituted carbamoyl groups, cyano group, nitro group, substituted or unsubstituted amino groups, alkyl groups (e.g., methyl, ethyl, isopropyl, t-butyl, hexyl, octyl, decyl, and other $C_1$-$C_{20}$ alkyl groups, of which $C_1$-$C_4$ alkyl groups are preferred), alkenyl groups, alkynyl groups, cycloalkyl groups, cycloalkenyl groups, aryl groups (e.g., phenyl, and naphthyl groups), aralkyl groups (e.g., benzyl group), and heterocyclic groups. An aromatic or non-aromatic carbon ring or heterocyclic ring may be condensed with the cycloalkane ring of the cycloalkanes within ranges not adversely affecting the reaction. The cycloalkanes can therefore be bridged hydrocarbons.

A corresponding cycloalkanol and/or a cycloalkanone may be added to a reaction system in addition to the cycloalkane. These compounds can be converted into a corresponding dicarboxylic acid.

Oxygen

As oxygen, any of molecular oxygen and nascent oxygen can be used. Such molecular oxygen is not specifically limited and includes pure oxygen, air, and oxygen diluted with an inert gas such as nitrogen gas, helium gas, argon gas, and carbon dioxide gas. Oxygen can be formed in the reaction system. The amount of oxygen varies depending on the type of the substrate but is generally equal to or more than 0.5 mole (e.g., equal to or more than 1 mole), preferably from about 1 to about 100 moles, and more preferably from about 2 to about 50 moles per mole of the substrate. Excess moles of oxygen to the substrate is often used. Molecular oxygen can be supplied to a gas phase or a liquid phase in the reactor.

Catalysts

Catalysts for use in the present invention are not specifically limited as long as they are oxidation catalysts that can convert cycloalkanes into corresponding dicarboxylic acids. Preferred catalysts include cobalt compounds, manganese compounds, and other transition metal compounds. The cobalt compounds include, but are not limited to, cobalt formate, cobalt acetate, cobalt propionate, cobalt naphthenate, cobalt stearate, cobalt lactate, and other organic acid salts; cobalt hydroxide, cobalt oxide, cobalt chloride, cobalt bromide, cobalt nitrate, cobalt sulfate, cobalt phosphate, and other inorganic compounds; acetylacetonatocobalt, other complexes, and other divalent or trivalent cobalt compounds. The manganese compounds include, but are not limited to, manganese formate, manganese acetate, manganese propionate, manganese naphthenate, manganese stearate, manganese lactate, and other organic acid salts; manganese hydroxide, manganese oxide, manganese chloride, manganese bromide, manganese nitrate, manganese sulfate, manganese phosphate, and other inorganic compounds; acetylacetonatomanganese, other complexes, and other divalent or trivalent manganese compounds. Each of these transition metal compounds can be used alone or in combination. Among them, cobalt compounds, manganese compounds, and mixtures of these compounds are preferred.

When such a transition metal compound is used as the catalyst, the amount thereof is, for example, from about 1 to about 200 mmol, and preferably from about 5 to about 100 mmol per kg of the total charged liquid.

Imide Compounds

Imide compounds having a cyclic imide skeleton represented by Formula (I) can also be used as the catalyst in the present invention. The imide compound can be used in combination with transition metal compound(s) such as the cobalt compound and/or manganese compound. The combination use of the imide compound with the transition metal compound as the catalyst may significantly improve the rate and/or selectivity of the reaction.

The bond between the nitrogen atom and X in Formula (I) is a single or double bond. The imide compound may have a plurality of the N-substituted cyclic imide skeleton represented by Formula (I). When X is a —OR group and $R^6$ is a hydroxyl-protecting group, a plurality of skeletons (N-oxy cyclic imide skeletons) derived from the N-substituted cyclic imide skeleton by removal of R may be combined through R.

The hydroxyl-protecting group R in Formula (I) includes conventional hydroxyl-protecting groups in the field of organic synthesis. Such protecting groups include, but are not limited to, alkyl groups (e.g., methyl, t-butyl, and other $C_1$-$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, 1-hydroxyalkyl groups (e.g., 1-hydroxyethyl, 1-hydroxyhexyl, 1-hydroxydecyl, 1-hydroxyhexadecyl, 1-hydroxy-1-phenylmethyl groups), and other groups that can form an acetal or hemiacetal group with a hydroxyl group; acyl groups (e.g., formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, stearoyl, and other aliphatic $C_1$-$C_{20}$ acyl groups, and other aliphatic unsaturated or saturated acyl groups; acetoacetyl group; cyclopentanecarbonyl, cyclohexanecarbonyl, other cycloalkanecarbonyl groups, and other alicyclic acyl groups; benzoyl, naphthoyl, and other aromatic acyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., methoxycarbonyl, ethoxycarbonyl, t-butoxycarbonyl, and other $C_1$-$C_4$ alkoxy-carbonyl groups), aralkyloxycarbonyl groups (e.g., benzyloxycarbonyl, and p-methoxybenzyloxycarbonyl groups), substituted or unsubstituted carbamoyl groups (e.g., carbamoyl, methylcarbamoyl, and phenylcarbamoyl groups), groups derived from inorganic acids (e.g., sulfuric acid, nitric acid, phosphoric acid, and boric acid) by removal of OH group, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

When X is a —OR group, a plurality of skeletons (N-oxy cyclic imide skeletons) derived from the N-substituted cyclic imide skeleton by removal of R may be combined through R. In this case, R includes, for example, oxalyl, malonyl, succinyl, glutaryl, adipoyl, phthaloyl, isophthaloyl, terephthaloyl, and other polycarboxylic acyl groups; carbonyl group; methylene, ethylidene, isopropylidene, cyclopentylidene, cyclohexylidene, benzylidene, and other polyvalenthydro carbon groups, of which groups that can form an acetal bond with two hydroxyl groups are preferred.

Preferred examples of R are hydrogen atom; groups that can form an acetal or hemiacetal group (bond) with a hydroxyl group; acyl groups, sulfonyl groups, alkoxycarbonyl groups, carbamoyl groups, and other groups derived from acids (e.g., carboxylic acids, sulfonic acids, carbonic acid, carbamic acid, sulfuric acid, phosphoric acids, and boric acids) by removal of OH group, and other hydrolyzable protecting groups that can be eliminated by hydrolysis.

In Formula (I), n is 0 or 1. Specifically, Formula (I) represents a five-membered N-substituted cyclic imide skeleton when n is 0 and represents a six-membered N-substituted cyclic imide skeleton when n is 1.

Typical examples of the imide compounds are imide compounds represented by Formula (1). In the substituents $R^1$, $R^2$, $R^3$, $R^4$, $R^5$, and $R^6$ in the imide compounds of Formula (1), the halogen atoms include iodine, bromine, chlorine, and fluorine atoms. The alkyl groups include, for example, methyl, ethyl, propyl, isopropyl, butyl, isobutyl, s-butyl, t-butyl, hexyl, decyl, dodecyl, tetradecyl, hexadecyl, and other straight- or branched-chain alkyl groups each containing from about 1 to about 30 carbon atoms, of which those each containing from about 1 to about 20 carbon atoms are preferred.

The aryl groups include, for example, phenyl and naphthyl groups. The cycloalkyl groups include, for example, cyclopentyl and cyclohexyl groups. The alkoxy groups include, for example, methoxy, ethoxy, isopropoxy, butoxy, t-butoxy, hexyloxy, octyloxy, decyloxy, dodecyloxy, tetradecyloxy, octadecyloxy, and other alkoxy groups each containing from about 1 to about 30 carbon atoms, of which alkoxy group search containing from about 1 to about 20 carbon atoms are preferred.

The substituted oxycarbonyl groups include, but are not limited to, methoxycarbonyl, ethoxycarbonyl, isopropoxycarbonyl, butoxycarbonyl, t-butoxycarbonyl, hexyloxycarbonyl, decyloxycarbonyl, hexadecyloxycarbonyl, and other $C_1$-$C_{30}$ alkoxy-carbonyl groups, of which $C_1$-$C_{20}$ alkoxy-carbonyl groups are preferred; cyclopentyloxycarbonyl, cyclohexyloxycarbonyl, and other cycloalkyloxycarbonyl groups, of which cycloalkyloxycarbonyl groups each having 3 to 20 members are preferred; phenyloxycarbonyl, naphthyloxycarbonyl, and other aryloxycarbonyl groups, of which $C_6$-$C_{20}$ aryloxy-carbonyl groups are preferred; benzyloxycarbonyl, and other aralkyloxycarbonyl groups, of which $C_7$-$C_{21}$ aralkyloxy-carbonyl groups are preferred.

The acyl groups include, but are not limited to, formyl, acetyl, propionyl, butyryl, isobutyryl, valeryl, pivaloyl, hexanoyl, octanoyl, decanoyl, lauroyl, myristoyl, palmitoyl, stearoyl, and other aliphatic $C_1$-$C_{30}$ acyl groups, of which aliphatic $C_1$-$C_{20}$ acyl groups are preferred, and other unsaturated or saturated aliphatic acyl groups; acetoacetyl group; cyclopentanecarbonyl, cyclohexanecarbonyl, and other cycloalkanecarbonyl, and other alicyclicacyl groups; benzoyl, naphthoyl, and other aromatic acyl groups.

The acyloxy groups include, but are not limited to, formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, stearoyloxy, and other aliphatic $C_1$-$C_{30}$ acyloxy groups, of which $C_1$-$C_{20}$ acyloxy groups are preferred, and other unsaturated or saturated aliphatic acyloxy groups; acetoacetyloxy group; cyclopentanecarbonyloxy, cyclohexanecarbonyloxy, and other cycloalkanecarbonyloxy, and other alicyclic acyloxy groups; benzoyloxy, naphthoyloxy, and other aromatic acyloxy groups.

The substituents $R^1$, $R^2$, $R^3$, $R^4$, $R^5$, and $R^6$ may be the same with or different from one another. At least two of $R^1$, $R^2$, $R^3$, $R^4$, $R^5$, and $R^6$ in Formula (1) may be combined to form a double bond, an aromatic ring, or a non-aromatic ring. The aromatic or non-aromatic ring has preferably from about 5 to about 12 members and more preferably from about 6 to about 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring often comprises an aromatic ring. The ring may have a substituent. Such substituents include, but are not limited to, alkyl groups, haloalkyl groups, hydroxyl group, alkoxy groups, carboxyl group, substituted oxycarbonyl groups, acyl groups, acyloxygroups, nitro group, cyano group, amino group, and halogen atoms.

One or more of the N-substituted cyclic imido group indicated in Formula (1) may be further formed on at least one of $R^1$, $R^2$, $R^3$, $R^4$, $R^5$, and $R^6$ and/or on the double bond, aromatic ring, or non-aromatic ring formed by the at least two of $R^1$, $R^2$, $R^3$, $R^4$, $R^5$, and $R^6$. For example, when at least one of $R^1$, $R^2$, $R^3$, $R^4$, $R^5$, and $R^6$ is an alkyl group containing two or more carbon atoms, the N-substituted cyclic imido group may be formed with the adjacent two carbon atoms constituting the alkyl group. Likewise, when at least two of $R^1$, $R^2$, $R^3$, $R^4$, $R^5$, and $R^6$ are combined to form a double bond, the N-substituted cyclic imido group may be formed with the double bond. When at least two of $R^1$, $R^2$, $R^3$, $R^4$, $R^5$, and $R^6$ are combined to form an aromatic or non-aromatic ring, the N-substituted cyclic imido group may be formed with the adjacent two carbon atoms constituting the ring.

Preferred imide compounds include compounds represented by following formulae:

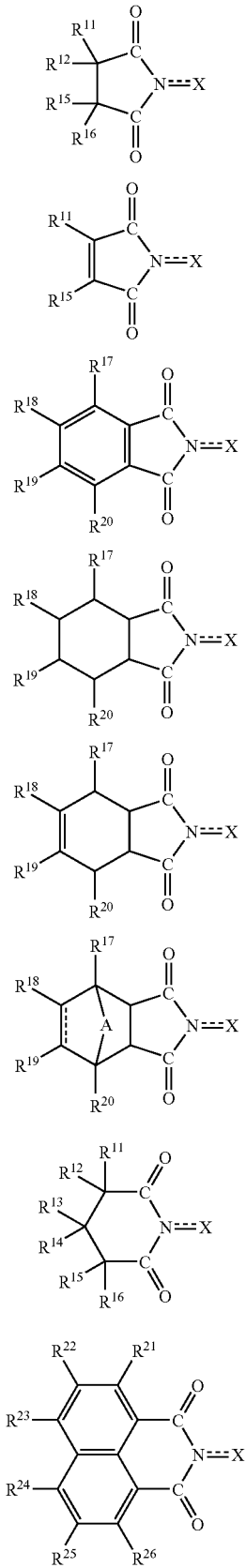

(1a)
(1b)
(1c)
(1d)
(1e)
(1f)
(1g)
(1h)

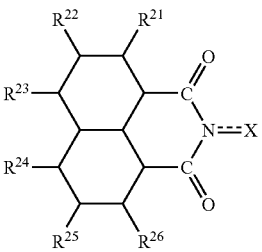

(1i)

wherein $R^{11}$, $R^{12}$, $R^{13}$, $R^{14}$, $R^{15}$, and $R^{16}$ are the same or different and are each one of hydrogen atom, halogen atoms, alkyl groups, aryl groups, cycloalkyl groups, hydroxyl group, alkoxy groups, carboxyl group, substituted oxycarbonyl groups, acyl groups, and acyloxy groups;

$R^{17}$, $R^{18}$, $R^{19}$, $R^{20}$, $R^{21}$, $R^{22}$, $R^{23}$, $R^{24}$, $R^{25}$, and $R^{26}$ are the same or different and are each one of hydrogen atom, alkyl groups, haloalkyl groups, hydroxyl group, alkoxygroups, carboxylgroup, substituted oxycarbonyl groups, acyl groups, acyloxy groups, nitro group, cyano group, amino group, and halogen atoms, wherein adjacent two of $R^{17}$ to $R^{26}$ may be combined to form a five- or six-membered N-substituted cyclic imide skeleton indicated in one of Formulae (1c), (1d), (1e), (1f), (1h), and (1i); and X has the same meaning as defined above.

The halogen atoms, alkyl groups, aryl groups, cycloalkyl groups, hydroxyl group, alkoxy groups, carboxyl group, substituted oxycarbonyl groups, acyl groups, and acyloxy groups in the substituents $R^{11}$ to $R^{16}$ include the same groups as in the corresponding groups in the substituents $R^1$ to $R^6$.

In the substituents $R^{17}$ to $R^{26}$, the alkyl groups include the same alkyl groups as those exemplified above, of which alkyl groups each containing from about 1 to about 6 carbon atoms are preferred. The haloalkyl groups include, for example, trifluoromethyl group, and other haloalkyl groups each containing from about 1 to about 4 carbon atoms. The alkoxy groups include the same alkoxy groups as those exemplified above, of which lower alkoxy groups each containing from about 1 to about 4 carbon atoms are preferred. The substituted oxycarbonyl groups include the same substituted oxycarbonyl groups as those exemplified above, such as alkoxy carbonyl groups, cycloalkyloxycarbonyl groups, aryloxycarbonyl groups, and aralkyloxycarbonyl groups. The acyl groups include aliphatic unsaturated or saturated acyl groups, acetoacetyl group, alicyclic acyl groups, aromatic acyl groups, and other acyl groups as exemplified above. The acyloxy groups include aliphatic unsaturated or saturated acyloxy groups, acetoacetyloxy group, alicyclic acyloxy groups, aromatic acyloxy groups, and other acyloxy groups as exemplified above. The halogen atoms include, for example, fluorine, chlorine, and bromine atoms. Each of the substituents $R^{17}$ to $R^{26}$ is often one of hydrogen atom, lower alkyl groups each containing from about 1 to about 4 carbon atoms, carboxyl group, substituted oxycarbonyl groups, nitro group, and halogen atoms.

Examples of preferred imide compounds having a five-membered N-substituted cyclic imide skeleton are N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β-tetramethylsuccinimide, N-hydroxymaleimide, N-hydroxyhexahydrophthalimide, N,N'-dihydroxycyclohexanetetracarboxylic diimide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauryloxy)succinimide, α,β-bis(benzoyloxy)-N-hydroxysuccinimide, N-hydroxy-4-methoxycarbonylphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N-hydroxyphthalimide, N-hydroxy-4,5-bis(pentyloxycarbonyl)phthalimide, 4,5-bis(dodecyloxycarbonyl)-N-hydroxyphthalimide, N-hydroxy-4,5-bis(phenoxycarbonyl)phthalimide, and other compounds of Formula (1) wherein X is a —OR group and R is a hydrogen atom; compounds corresponding to these compounds except with R of an acyl group such as acetyl group, propionyl group, and benzoyl group; N-methoxymethyloxyphthalimide, N-(2-methoxyethoxymethyloxy)phthalimide, N-tetrahydropyranyloxyphthalimide, and other compounds of Formula (1) wherein X is a —OR group and R is a group that can form an acetal or hemiacetal bond with a hydroxyl group; N-methanesulfonyloxyphthalimide, N-(p-toluenesulfonyloxy)phthalimide, and other compounds of Formula (1) wherein X is a —OR group and R is a sulfonyl group; sulfuric esters, nitric esters, phosphoric esters, and boric esters of N-hydroxyphthalimide, and other compounds of Formula (1) wherein X is a —OR group and R is a group derived from an inorganic acid by removal of OH group.

Examples of preferred imide compounds having a six-membered N-substituted cyclic imide skeleton are N-hydroxyglutarimide, N-hydroxy-α,α-dimethylglutarimide, N-hydroxy-β,β-dimethylglutarimide, N-hydroxy-1,8-decalindicarboximide, N,N'-dihydroxy-1,8;4,5-decalintetracarboxylic diimide, N-hydroxy-1,8-naphthalenedicarboximide (N-hyrdoxynaphthalimide), N,N'-dihydroxy-1,8;4,5-naphthalenetetracarboxylic diimide, and other compounds of Formula (1) wherein X is a —OR group and R is a hydrogen atom; compounds corresponding to these compounds except with R of an acyl group such as acetyl group, propionyl group, and benzoyl group; N-methoxymethyloxy-1,8-naphthalenedicarboximide, N,N'-bis(methoxymethyloxy)-1,8;4,5-naphthalenetetracarboxy lic diimide, and other compounds of Formula (1) wherein X is a —OR group and R is a group that can form an acetal or hemiacetal bond with a hydroxyl group; N-methanesulfonyloxy-1,8-naphthalenedicarboximide, N,N'-bis(methanesulfonyloxy)-1,8;4,5-naphthalenetetracarbo xylic diimide, and other compounds of Formula (1) wherein X is a —OR group and R is a sulfonyl group; sulfuric esters, nitric esters, phosphoric esters, and boric esters of N-hydroxy-1,8-naphthalenedicarboximide and N,N'-dihydroxy-1,8;4,5-naphthalenetetracarboxylic diimide, and other compounds of Formula (1) wherein X is a —OR group and R is a group derived from an inorganic acid by removal of OH group.

Among the imide compounds, compounds wherein X is a —OR group and R is ahydrogen atom (N-hydroxy cyclic imide compounds) can be prepared by a conventional imidization process such as a process that comprises the steps of allowing a corresponding acid anhydride to react with hydroxylamine for ring-opening of an acid anhydride group, and closing the ring to form an imide. Compounds of formula (1) wherein X is a —OR group and R is a hydroxyl-protecting group can be prepared by introducing a desired protecting group into a corresponding compound wherein R is a hydrogen atom (N-hydroxy cyclic imide compounds) by the aid of a conventional reaction for the introduction of protecting groups. For example, N-acetoxy phthalimide can be prepared by allowing N-hydroxyphthalimide to react with acetic anhydride or to react with an acetyl halide in the presence of a base. These compounds can also be prepared by other processes.

Typically preferred imide compounds are N-hydroxysuccinimide, N-hydroxyphthalimide, N,N'-dihydroxypyromellitic diimide, N-hydroxyglutarimide, N-hydroxy-1,8-naphthalenedicarboximide, N,N'-dihydroxy-1,8;4,5-naphthalenetetracarboxylic diimide, and other N-hydroxyimide compounds derived from alicyclic polycarboxylic anhydrides or aromatic polycarboxylic anhydrides; and compounds derived from the N-hydroxyimide compounds by introduction of a protecting group into hydroxyl groups thereof.

Each of the imide compounds having at least one N-substituted cyclic imide skeleton represented by Formula (I) can be used alone or in combination in the reaction. The imide compounds can be formed in a reaction system.

The amount of the imide compound(s) can be selected within broad ranges and is, for example, from about 0.0000001 to about 1 mole, preferably from about 0.000001 to about 0.5 mole, more preferably from about 0.00001 to about 0.4 mole, and often from about 0.0001 to about 0.35 mole, per mole of the cycloalkane (substrate). The amount of the imide compound(s) is, for example, from about 0.0000006 to about 6 moles, and preferably from about 0.0006 to about 2.1 moles per kg of the total charged liquid.

Promoters (Co-Catalysts)

A promoter (a co-catalyst) can be used in the reaction. The combination use of the catalyst with the promoter can improve or enhance the rate and/or selectivity of the reaction. Such promoters include, for example, organic salts comprising a polyatomic cation or a polyatomic anion and its counter ion, which polyatomic cation or anion contains a Group 15 or Group 16 element of the Periodic Table of Elements having at least one organic group combined therewith.

In the organic salts, the Group 15 elements of the Periodic Table of Elements include N, P, As, Sb, and Bi, and the Group 16 elements of the Periodic Table of Elements include, for example, O, S, Se and Te. Preferred elements are N, P, As, Sb, and S, of which N, P, and S are typically preferred.

The organic groups to be combined with the atoms of elements include, but are not limited to, aliphatic hydrocarbon groups, alicyclic hydrocarbon groups, aromatic hydrocarbon groups, and other hydrocarbon groups which may have a substituent; and alkoxy groups, aryloxy groups, aralkyloxy groups, and other substituted oxy groups.

Examples of the organic salts are organic ammonium salts, organic phosphonium salts, organic sulfonium salts, and other organic onium salts. Examples of organic ammonium salts include tetramethylammonium chloride, tetrabutylammonium chloride, triethylphenylammonium chloride, other quaternary ammonium chlorides, corresponding quaternary ammonium bromides, and other quaternary ammonium salts each having four hydrocarbon groups combined with its nitrogen atom; dimethylpiperidinium chloride, hexadecylpyridinium chloride, methylquinolinium chloride, and other cyclic quaternary ammonium salts. Examples of the organic phosphonium salts include tetramethylphosphonium chloride, tetrabutylphosphonium chloride, other quaternary phosphonium chlorides, corresponding quaternary phosphonium bromides, and other quaternary phosphonium salts each having four hydrocarbon groups combined with its phosphorus atom. Examples of the organic sulfonium salts include triethylsulfonium iodide, ethyldiphenylsulfonium iodide, and other sulfonium salts each having three hydrocarbon groups combined with its sulfur atom.

The organic salts also include methanesulfonates, dodecanesulfonates, and other alkyl-sulfonates (e.g., $C_1$-$C_{18}$ alkyl-sufonates); benzenesulfonates, p-toluenesulfonates, naphthalenesulfonates, and other aryl-sulfonates which may be substituted with an alkyl group (e.g., $C_1$-$C_{18}$ alkyl-arylsufonates); sulfonic acid type ion exchange resins (ion exchangers); and phosphonic acid type ion exchange resins (ion exchangers).

The amount of the organic salt(s) is, for example, from about 0.001 to about 0.1 mole, and preferably from about 0.005 to about 0.08 mole per mole of the catalyst.

Strong acids such as compounds having a pKa of less than or equal to 2 (at 25° C.) can also be used as the promoter. Preferred examples of strong acids are hydrogen halides, hydrohalogenic acids, sulfuric acid, and heteropolyacids. The amount of the strong acid(s) is, for example, from about 0.001 to about 3 moles per mole of the catalyst.

The promoters for use in the present invention also include compounds having a carbonyl group combined with an electron attractive group. Examples of such compounds are hexafluoroacetone, trifluoroacetic acid, pentafluorophenyl (methyl) ketone, pentafluorophenyl (trifluoromethyl) ketone, and benzoic acid. The amount of the compound(s) is, for example, from about 0.0001 to about 3 moles per mole of the cycloalkane (substrate).

The reaction system may further comprise a free-radical generator or a free-radical reaction accelerator. Such components include, but are not limited to, halogens (e.g., chlorine and bromine), peracids (e.g., peracetic acid and m-chloroperbenzoic acid), and peroxides (e.g., hydrogen peroxide, t-butyl hydroperoxide (TBHP), and other hydroperoxides), nitric acid, nitrous acid, and salts thereof, nitrogen dioxide, benzaldehyde, and other aldehydes. The existence of the component(s) in the system may enhance a reaction. The amount of the aforementioned component(s) is, for example, from about 0.001 to about 3 mole per mole of the catalyst.

Reactions

The reaction is performed in a liquid phase using a continuous reactor. A reaction vessel in the reactor can be of any type such as a complete mixing vessel and a plug flow vessel.

Reaction solvents for use in the present invention include, but are not limited to, benzene and other aromatic hydrocarbons; dichloromethane, chloroform, 1,2-dichloroethane, dichlorobenzene, and other halogenated hydrocarbons; t-butyl alcohol, t-amyl alcohol, and other alcohols; acetonitrile, benzonitrile, and other nitriles; acetic acid, propionic acid, and other carboxylic acids; formamide, acetamide, dimethylformamide (DMF), dimethylacetamide, and other amides. Each of these solvents can be used alone or in combination. The reaction product dicarboxylic acid can also be used as the reaction solvent. Among the solvents, carboxylic acids and other organic protonic solvents as well as nitriles are preferred, of which acetic acid, and other carboxylic acids are typically preferred. The reaction may be performed without supply of the reaction solvent.

One of the features of the present invention is that a residence time $\tau$ (hr) in the continuous reactor is set so as to satisfy the following condition:

$$0.1 \leq \tau \leq 50/c$$

wherein c is the proportion (% by weight) of the cycloalkane based on the total weight of the charged liquid (the total of the cycloalkane, solvent, catalyst, and other components).

The residence time $\tau$ (hr) can be determined by calculation according to the following equation.

$$\tau \text{ (hr)} = [\text{Amount of liquid in the reaction vessel (L)}] / [\text{Flow rate of the charged liquid (L/hr)}]$$

If the residence time is shorter than 0.1 hour, the conversion from the cycloalkane decreases. With a gradually increasing residence time from 0.1 hour, the conversion from the cycloalkane gradually increases. However, from a certain midpoint, other dicarboxylic acids than the target dicarboxylic acid (a dicarboxylic acid with a carbon chain containing carbon atoms in the same number as the carbon atoms constituting the cycloalkane ring), i.e., dicarboxylic acids each with a carbon chain containing carbon atom(s) in a number one or more less than that of the carbon atoms constituting the cycloalkane ring, increase, and the reactivity decreases. As a result, the space-time yield (STY) of the target dicarboxylic acid significantly decreases.

For example, when the residence time is increased in the production of adipic acid by oxidation of cyclohexane using a continuous reactor, the reactivity decreases at or above some middle point, and the selectivity of adipic acid on the basis of total dicarboxylic acids (the total of adipic acid, glutaric acid, and succinic acid) gradually decreases. With an increasing residence time, by-products such as hydroxycaproic acid, butyrolactone, and valerolactone increase, but at or above some midpoint, these by-produced compounds decrease. These results suggest that the by-products convert to other substances in such a long-time reaction, and some of the converted substances may adversely affect the activity of the catalyst such as a cobalt compound or manganese compound. Japanese Unexamined Patent Application Publication No. 50-8790 describes that when cyclohexane is oxidized with oxygen in a batch system and a cobalt compound catalyst is reused over again, the catalytic activity gradually decreases, and the catalyst having the decreased activity is activated by treatment with an organic solvent. These suggest that the inhibitor is an organic compound and poisons the catalytic metal to thereby deteriorate the catalytic activity by, for example, the formation of a metallic complex.

An optimum residence time varies depending on the ratio of the cycloalkane to the total charged liquid supplied to the reaction vessel (concentration of the cycloalkane in the charged liquid). If the concentration of the cycloalkane in the charged liquid is high, a cycloalkane phase separates from an aqueous phase in the reaction system with a slightly increasing residence time due to water formed during the reaction, and the reactivity rapidly decreases. The residence time immediately before the rapid decrease of the reactivity is an optimum residence time in this case. If the cycloalkane concentration in the charged liquid is low and the cycloalkane phase does not separate from the aqueous phase in the reaction system, the reactivity decreases due to the reaction inhibitor with an increasing residence time. In this case, the residence time immediately before the decrease of the selectivity of the target dicarboxylic acid on the basis of the total dicarboxylic acids is an optimum residence time. These findings show that the upper limit of a preferred residence time is substantially inversely proportional to the cycloalkane concentration in the charged liquid and is expressed by 50/c, wherein c has the same meaning as defined above.

The lower and upper limits of the residence time are preferably 0.2 hour and 40/c, wherein c has the same meaning as defined above, respectively. The concentration c is preferably equal to or more than 15% by weight (e.g., from 15% to 99.5% by weight), more preferably equal to or more than 18% by weight (e.g., from 18% to 95% by weight), more preferably equal to or more than 20% by weight (e.g., from 20% to 80% by weight), and typically preferably equal to or more than 25% by weight (e.g., from 25% to 60% by weight). If the concentration c is excessively low, the conversion speed of the cycloalkane may become excessively low, and the space-time yield (yield per unit volume and per unit time) of the produced dicarboxylic acid may decrease.

The present inventors have found that, when a cobalt compound is used as the catalyst, the ratio of Co(II) to Co(III) in the reaction mixture is substantially invariant of about 90:10 regardless of the residence time. It is believed that Co(III) exhibits catalytic activity and Co(II) does not in oxidation reactions of cycloalkanes (e.g., Kogyo Kagaku Zasshi (Journal of the Chemical Society of Japan, Industrial chemistry section), 72(12), 2590 (1969)). The fact that the ratio of Co(II) to Co(III) in the reaction system is invariant indicates that cobalt is poisoned without changing its oxidation number and decreases in its reaction activity by, for example, forming a complex with the reaction inhibitor.

A reaction temperature is, for example, from 80° C. to 200° C., preferably from 80° C. to 150° C., and more preferably from 90° C. to 140° C. If the reaction temperature is lower than 80° C., the reaction rate (reaction speed) may decrease. If it is excessively high, the selectivity of the target dicarboxylic acid may often decrease. The reaction can be performed at atmospheric pressure or under a pressure (under a load). When the reaction is performed under a pressure, the reaction pressure is, for example, equal to or more than about 0.5 MPa (e.g., from about 0.5 to about 20 MPa), and preferably from about 1 to about 15 MPa.

As a result of the reaction, the material cycloalkane oxidatively cleaves and thereby mainly yields a dicarboxylic acid with a carbon chain containing carbon atoms in the same number as carbon atoms constituting the cycloalkane ring. Specifically, cyclohexane yields adipic acid, and cyclododecane yields a dodecanedicarboxylic acid. Under some conditions, dicarboxylic acids with a carbon chain containing carbon atoms in a number one or two less than the number of carbon atoms constituting the cycloalkane ring, and/or corresponding cycloalkanols and cyckoalkanones may be by-produced. For example, glutaric acid, succinic acid, cyclohexanol, cyclohexanone, acetic acid, cyclohexyl acetate, lactones such as butyrolactone and valerolactone, adipic esters, and/or hydroxycaproic acid may be by-produced from material cyclohexane. Among these by-products, cycloalkanols and cycloalkanones can be recycled into the reaction system.

The reaction product(s) can be separated and purified by separation means such as filtration, concentration, distillation, extraction, crystallization, recrystallization, adsorption, column chromatography, and combinations thereof.

Dicarboxylic acids obtained by the production process of the present invention can be used as, for example, raw materials for polyamides (nylons) and polyesters, additives for polymers such as polyurethanes, and intermediate materials for fine chemicals.

EXAMPLES

The present invention will be illustrated in further detail with reference to several examples and comparative examples below, which are not intended to limit the scope of the invention. Products in the examples and comparative examples were analyzed by gas chromatography and high-performance liquid chromatography. In the following tables, the abbreviations CHX, STY, and ADA mean cyclohexane, the space-time yield (kg-ADA/m$^3$·hr) and adipic acid, respectively.

Examples 1 to 3 and Comparative Example 1

Cyclohexane (CHX), acetic acid (AcOH), and cobalt(II) acetate and N-acetoxy phthalimide as catalysts were continuously supplied to a 1000-ml reactor made of titanium equipped with a three-stage puddle agitator (revolutions: 500 rpm) so that the residence time τ (hr) was a set value. The residence time was controlled by changing the supply amount of the materials. The materials were supplied in two lines, a line for supplying cyclohexane and a line for supplying a solution of the catalysts in acetic acid. These material supply lines meet with each other at an inlet of the reactor, and the materials were supplied from the top of the reactor through an insertion tube to a liquid phase.

The weight ratio of supplied cyclohexane CHX to supplied acetic acid AcOH is 30/70. The amounts of cobalt(II) acetate and N-acetoxy phthalimide were 21 mmol/kg and 23 mmol/kg, respectively, relative to the total weight of the charged materials. The concentration c of cyclohexane to the total charged materials was 30% by weight. The results of reactions are shown in Table 1.

TABLE 1

|  | Residence Time (hr) | Conversion from CHX (%) | STY |
|---|---|---|---|
| Example 1 | 0.40 | 8.8 | 53.5 |
| Example 2 | 0.85 | 15.8 | 51.5 |
| Example 3 | 1.50 | 21.7 | 45.5 |
| Comparative Example 1 | 2.01 | 23.0 | 30.9 |

Table 1 shows that adipic acid is obtained in high space-time yields according to Examples 1 to 3 in which the residence time τ satisfies the following condition: $0.1 \leq \tau \leq 1.7$ (=50/c) but is obtained in a markedly low space-time yield according to Comparative Example 1 in which the residence time τ does not satisfy the above condition.

Examples 4 to 6 and Comparative Example 2

Cyclohexane (CHX), acetic acid (AcOH), and cobalt(II) acetate as a catalyst were continuously supplied to a 1000-ml reactor made of titanium equipped with a three-stage puddle agitator (revolutions: 500 rpm) so that the residence time τ (hr) was a set value. The residence time was controlled by changing the supply amount of the materials. The materials were supplied in the same manner as in Examples 1 to 3 and Comparative Example 1.

The weight ratio of supplied cyclohexane CHX to supplied acetic acid AcOH is 30/70. The amount of cobalt(II) acetate was 21 mmol/kg relative to the total weight of the charged materials. The concentration c of cyclohexane to the total charged materials was 30% by weight. The results of reactions are shown in Table 2.

TABLE 2

|  | Residence Time (hr) | Conversion from CHX (%) | STY |
|---|---|---|---|
| Example 4 | 0.37 | 7.7 | 60.1 |
| Example 5 | 0.72 | 14.2 | 57.9 |
| Example 6 | 1.40 | 18.8 | 48.3 |
| Comparative Example 2 | 1.91 | 19.7 | 29.0 |

Table 2 shows that adipic acid is obtained in high space-time yields according to Examples 4 to 6 in which the residence time τ satisfies the following condition: 0.1≦τ≦1.7 (=50/c) but is obtained in a markedly low space-time yield according to Comparative Example 2 in which the residence time τ does not satisfy the above condition.

Example 7 and Comparative Example 3

The procedures of Examples 1 to 3 and Comparative Example 1 were repeated, except that the weight ratio of supplied cyclohexane to supplied acetic acid was changed to 60/40. The concentration c of cyclohexane to the total charged materials was 60% by weight. The results of reactions are shown in Table 3.

TABLE 3

|  | Residence Time (hr) | Conversion from CHX (%) | STY |
|---|---|---|---|
| Example 7 | 0.72 | 9.9 | 65.0 |
| Comparative Example 3 | 1.77 | 9.0 | 28.0 |

Table 3 shows that adipic acid is obtained in a high space-time yield according to Examples 7 in which the residence time τ satisfies the following condition: 0.1≦τ≦0.83 (=50/c) but is obtained in a markedly low space-time yield according to Comparative Example 3 in which the residence time τ does not satisfy the above condition.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing a dicarboxylic acid comprising the step of subjecting a cycloalkane to an oxidative cleavage reaction with oxygen in the presence of a catalyst comprising: a divalent or trivalent cobalt compound; or a divalent or trivalent cobalt compound and an imide compound having at least one cyclic imide skeleton represented by the following Formula (1)

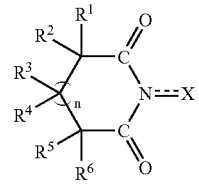

(1)

wherein n is 0 or 1; and
X is an oxygen atom or a —OR group,
wherein R is a hydrogen atom or a hydroxyl-protecting group, $R^1, R^2, R^3, R^4, R^5$ and $R^6$ are the same or different and are each one selected from the group consisting of a hydrogen atom, halogen atoms, alkyl groups, aryl groups, cycloalkyl groups, hydroxyl groups, alkoxy groups, carboxyl groups, substituted oxycarbonyl groups, acyl groups, and acyloxy groups,
wherein at least two of $R^1, R^2, R^3, R^4, R^5$ and $R^6$ may be combined to form one of a double bond, an aromatic ring and a non-aromatic ring, and
wherein one or more of the N-substituted cyclic imido groups indicated in Formula (1) may be formed on at least one of $R^1, R^2, R^3, R^4, R^5$ and $R^6$ and/or on the double bond, aromatic ring or non-aromatic ring formed by the at least two of $R^1, R^2, R_3, R^4, R^5$ and $R^6$,
in a liquid phase using a continuous reactor to thereby yield a corresponding dicarboxylic acid,
wherein the residence time τ (hr) satisfies the following condition:

$$0.1 \leq \tau \leq 50/c$$

wherein c is the proportion (% by weight) of the cycloalkane to the total weight of a charged liquid, with c being equal to or more than 25% by weight.

2. The process according to claim 1, further comprising performing the oxidative cleavage reaction in the presence of a carboxylic acid as a reaction solvent.

3. The process according to claim 1, further comprising performing the oxidative cleavage reaction at a reaction temperature of 80° C. to 150° C.

4. The process according to claim 1, further comprising performing the oxidative cleavage reaction at a reaction pressure of equal to or more than 0.5 MPa.

* * * * *